United States Patent [19]

Algieri et al.

[11] Patent Number: 4,692,531
[45] Date of Patent: Sep. 8, 1987

[54] SUBSTITUTED 3,4-DIAMINO-1,2,5-THIADIAZOLES HAVING HISTAMINE H₂-RECEPTOR ANTAGONIST ACTIVITY

[75] Inventors: Aldo A. Algieri, Fayetteville; Ronnie R. Crenshaw, Dewitt, both of N.Y.

[73] Assignee: Bristol-Myers Company, Wallingford, Conn.

[21] Appl. No.: 911,613

[22] Filed: Sep. 25, 1986

Related U.S. Application Data

[62] Division of Ser. No. 623,588, Jun. 22, 1984, Pat. No. 4,644,006.

[51] Int. Cl.⁴ .................................... C07D 277/48
[52] U.S. Cl. .................................... 548/193; 544/331; 544/333; 546/277; 546/278; 548/128; 548/131; 548/133; 548/134; 548/135; 548/143; 548/199; 548/202; 548/205; 548/337; 548/342
[58] Field of Search ............... 548/193, 128, 131, 133, 548/134, 135, 143, 199, 202, 205, 337, 342; 544/331, 333; 546/277, 278

[56] References Cited

U.S. PATENT DOCUMENTS

4,374,248  2/1983  Crenshaw ........................ 548/135
4,440,933  4/1984  Montzka .......................... 546/193

FOREIGN PATENT DOCUMENTS

40696  12/1981  European Pat. Off. ............ 548/134
45155   2/1982  European Pat. Off. ............ 548/134
60730   9/1982  European Pat. Off. ............ 548/134
65823  12/1982  European Pat. Off. ............ 548/134

*Primary Examiner*—Robert Gerstl
*Attorney, Agent, or Firm*—Aldo A. Algieri

[57] ABSTRACT

Histamine H₂-receptor antagonists of the formula

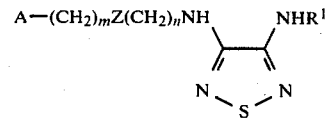

wherein A, m, Z, n and R¹ are as defined herein, and their nontoxic pharmaceutically acceptable salts are novel anti-ulcer agents which are prepared by ring closure of a substituted ethanediimidamide of the formula

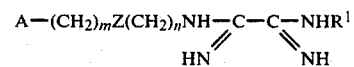

5 Claims, No Drawings

SUBSTITUTED 3,4-DIAMINO-1,2,5-THIADIAZOLES HAVING HISTAMINE H₂-RECEPTOR ANTAGONIST ACTIVITY

CROSS-REFERENCE TO RELATED APPLICATION

This application is a divisional of our prior, co-pending application Ser. No. 623,588, filed June 22, 1984, now U.S. Pat No. 4,644,006.

SUMMARY OF THE INVENTION

Certain 3-(amino or substituted amino)-4-(substituted amino)-1,2,5-thiadiazoles having the formula

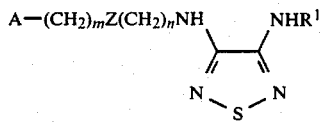

wherein A, m, Z, n and $R^1$ are as defined below, and their nontoxic pharmaceutically acceptable salts are potent histamine $H_2$-receptor antagonists which inhibit gastric acid secretion and are useful in the treatment of peptic ulcers and other pathological hypersecretory conditions. The compounds are prepared by ring closure of the correspondingly substituted ethanediimidamide of the formula

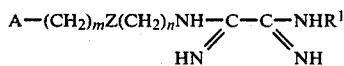

INFORMATION DISCLOSURE STATEMENT

Our U.S. Pat. No. 4,374,248 (R. R. Crenshaw and A. A. Algieri), issued Feb. 15, 1983, discloses 3,4-disubstituted-1,2,5-thiadiazole 1-oxides and 1,1-dioxides having the formula

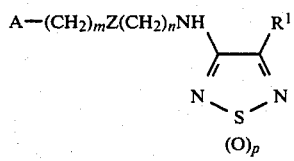

and processes for their preparation, wherein the variables A, m, Z, n and $R^1$ are similar to some of the corresponding substituents of the compounds disclosed and claimed herein. However, the compounds disclosed therein are 1-oxides or 1,1-dioxides (p is 1 or 2), and the compounds of the present invention cannot be prepared by any of the processes described therein for the preparation of the prior art compounds.

European Patent Application No. 40,696 published Dec. 2, 1981 discloses inter alia 3,4-disubstituted-1,2,5-thiadiazole 1-oxides and 1,1-dioxides having the formula

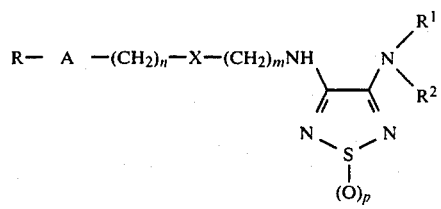

and processes for their preparation, wherein the variables R, A, n, X, m, $R^1$ and $R^2$ are similar to some of the corresponding substituents of the compounds disclosed and claimed herein. However, the compounds disclosed therein also are 1-oxides or 1,1-dioxides (p is 1 or 2) and the compounds of the present invention cannot be prepared by any of the processes described therein for the preparation of the prior art compounds.

European Patent Application No. 45,155 published Feb. 3, 1982 discloses an extremely large number of guanidine derivatives of the general formula

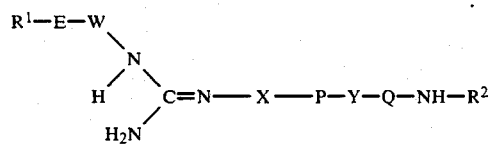

and processes for their preparation, wherein the variables $R^1$, E, W, X, P, Y, Q and $R^2$ correspond to a large number of substituents. In the compounds disclosed therein, $R^2$ is defined as a radical of the formula —A—B in which —A— is a large number of radicals wherein one of the radicals can be of the formula

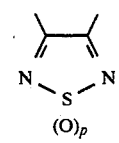

and p is 1 or 2. However, none of the compounds of the present invention are disclosed or can be prepared by any of the processes described therein.

European Patent Application No. 60,730 published Sept. 22, 1982 discloses an extremely large number of guanidine derivatives having the general formula

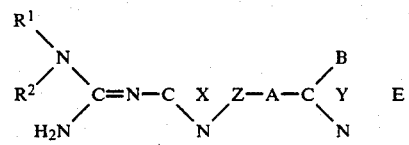

and processes for their preparation, wherein the variables $R^1$, $R^2$, X, Z, A, B, E and Y correspond to a large number of substituents. In the compounds disclosed therein, Y is defined as a large number of radicals wherein one of the radicals can be of the formula

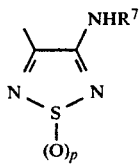

and p is 1 or 2 with the limitation that when an optional insertion is made in chain A which results in the inserted group being directly attached to ring Y, the inserted group is other than an NH or N-alkyl radical. However, none of the compounds of the present invention are disclosed or can be prepared by any of the processes described therein.

European Patent Application No. 65,823 published Dec. 1, 1982 discloses 3,4-disubstituted-1,2,5-thiadiazole 1-oxides and 1,1-dioxides having the formula

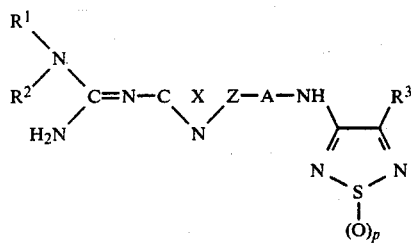

and processes for their preparation, wherein the variables $R^1$, $R^2$, X, Z, A and $R^3$ correspond to a large number of substituents. However, the compounds disclosed therein are 1-oxides or 1,1-dioxides (p is 1 or 2), and the compounds of the present invention cannot be prepared by any of the processes described therein.

Our U.K. patent application No. 2,117,769 (R. R. Crenshaw and A. A. Algieri), published Oct. 19, 1983, discloses 3,4-disubstituted-1,2,5-thiadiazoles having the formula

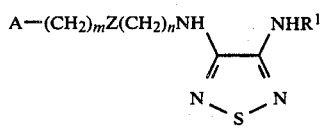

and processes for their preparation, wherein the variables m, Z, n and $R^1$ are similar to the corresponding substituents of the compounds disclosed and claimed herein. However, in the compounds disclosed therein, A is a radical having the formula

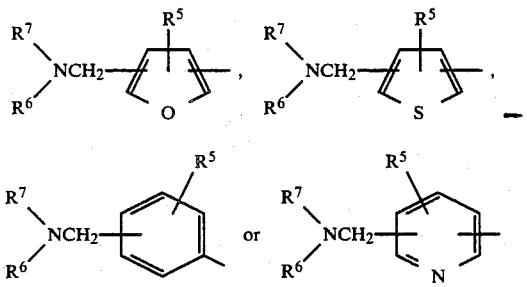

and none of the compounds of the present invention are disclosed therein.

U.S. Pat. No. 4,440,933 (T. A. Montzka), issued Apr. 3, 1984, discloses a process for the preparation of compounds having the formula

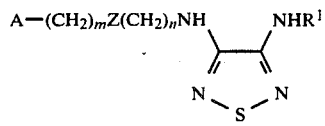

wherein the variables A, m, Z, n and $R^1$ are substantially the same as the substituents disclosed in the above-mentioned published U.K. patent application No. 2,117,769, and none of the compounds of the present invention are disclosed therein.

COMPLETE DISCLOSURE

This application relates to histamine $H_2$-receptor antagonists which are effective inhibitors of gastric acid secretion in animals, including man, which are useful in the treatment of peptic ulcers and other conditions caused or exacerbated by gastric acidity, and which have the formula

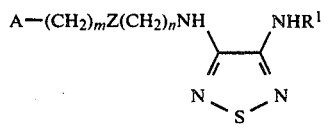

wherein $R^1$ is hydrogen, (lower)alkyl, 2-fluoroethyl, 2,2,2-trifluoroethyl, allyl, propargyl,

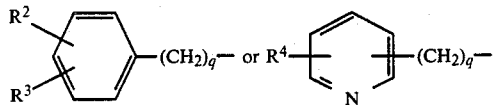

in which q is 1 or 2, $R^2$ and $R^3$ each are independently hydrogen, (lower)alkyl, (lower)alkoxy or halogen, and, when $R^2$ is hydrogen, $R^3$ also may be trifluoromethyl, or $R^2$ and $R^3$, taken together, may be methylenedioxy, and $R^4$ is hydrogen, (lower)alkyl or (lower)alkoxy;

m is an integer of from 0 to 2 inclusive;

n is an integer of from 2 to 5 inclusive;

Z is oxygen, sulfur or methylene; and

A is a 5- or 6-membered heterocyclic ring containing at least one nitrogen atom and one or two additional heteroatoms independently selected from oxygen, sulfur and nitrogen; provided that A may contain one or two substituents, the first substituent being selected from

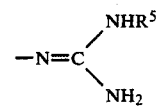

or $-CH_2NR^6R^7$ and the second substituent selected from (lower)alkyl, halogen or (lower)alkoxy;

$R^5$ is hydrogen, branched or unbranched (lower)alkyl, (lower)cycloalkyl, or (lower)cycloalkyl(lower)alkyl, in which $R^5$ may optionally contain one or more halogen atoms selected from flourine, chlorine and bromine, provided that there is no halogen substituent on the carbon atom directly attached to the nitrogen atom;

R[6] and R[7] each are independently hydrogen or (lower)alkyl, or, R[6] and R[7], taken together with the nitrogen to which they are attached, may be pyrrolidino, methypyrrolidino, piperidino, methypiperidino, homopiperidino or heptamethyleneimino, and a nontoxic pharmaceutically acceptable salt thereof.

This application also relates to processes for the preparation of the compounds of Formula I and to intermediates in the preparation of the compounds of Formula I.

The present invention includes within its scope all possible tautomeric forms, geometric isomers, optical isomers and zwitterionic forms of the compounds of Formula I, as well as mixtures thereof. As used herein and in the claims (unless the context indicates otherwise), the terms "(lower)alkyl" and "(lower)alkoxy" mean unbranched or branched chain alkyl or alkoxy groups containing from 1 to 6 carbon atoms. Preferably these groups contain from 1 to 4 carbon atoms and, most preferably, they contain 1 or 2 carbon atoms. The term "cyclo(lower)alkyl", as used herein and in the claims, means a cycloalkyl ring containing from 3 to 7 carbon atoms and preferably from 3 to 6 carbon atoms. Unless otherwise specified in the particular instance, the term "halogen" as used herein and in the claims is intended to include chloride, flourine, bromine and iodine. The term "nontoxic pharmaceutically acceptable salts" is intended to include salts of the compounds of formula I with any nontoxic pharmaceutically acceptable acid. Such acids are well-known and include hydrochloric, hydrobromic, sulfuric, sulfamic, phosphoric, nitric, maleic, fumaric, succinic, oxalic, benzoic, methanesulfonic, tartaric, citric, levulinic, camphorsulfonic and the like. The salts are made by methods known in the art.

In the compounds of Formula I, R[1] preferably is hydrogen or (lower)alkyl. Substituent A preferably is the substituted imidazole moiety, substituted thiazole moiety, substituted thiadiazole moiety, substituted oxazole moiety, substituted oxadiazole moiety or substituted pyrimidine moiety shown above, more preferably is substituted thiazole moiety or subsitituted pyrimidene moiety, and most preferably is the substituted thiazole moiety. Substituent Z preferably is sulfur or oxygen. It is preferred that m is zero or 1 and n is 2 or 3. R[2], and R[3] and R[4] preferably are hydrogen or (lower)alkyl, or R[2] and R[3], taken together, is methylenedioxy. It is preferred that q is 1. Substituent R[5] preferably is hydrogen, or unbranched (lower)alkyl, in which R[5] may contain one or more halogen atoms, provided that there is no halogen substituent on the carbon atom directly attached to the nitrogen atom. R[6] and R[7] preferably are (lower)alkyl or, taken together with the nitrogen atom to which they are attached, are pyrrolidino or piperidino.

The compounds of Formula I may be prepared by reaction of the correspondingly substituted ethanediimidamide of the Formula II with sulfur monochloride (S₂Cl₂), sulfur dichloride (SCl₂), R—S—R (Formula III) or chemical equivalents thereof, as follows:

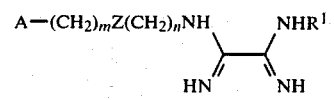

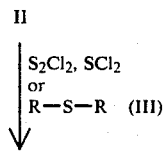

wherein A, m, Z, n and R[1] are as defined above, and R is as defined below.

In reacting a compound of Formula II with S₂Cl₂ or SCl₂, at least about 1 mole of S₂Cl₂ or SCl₂ should be used per mole of Compound II; it is preferred to use an excess of S₂Cl₂ or SCl₂, e.g. from about 2 to about 3 moles of S₂Cl₂ or SCl₂ per mole of Compound II. The reaction temperature is not critical; we prefer to conduct the reaction at a temperature of from about 0° C. to about 50° C., and it is most convenient to conduct the reaction at ambient temperature. The reaction time is not critical and is dependent on temperature. We normally utilize a reaction time of from about 30 minutes to about 6 hours. At ambient temperature, reaction times of from about 1½ to 4 hours usually are preferred. The reaction may be conducted in an inert organic solvent, preferably a mixture of an inert organic solvent and dimethylformamide. Most preferably the reaction is conducted in dimethylformamide.

In reacting a compound of Formula II with a sulfur compound of Formula III, the reaction ratio is not critical. It is preferred to use at least an equimolar amount of the compound of Formula III, but an excess may be utilized. It is most preferred to conduct the reaction with about an equimolar amount of Compounds II and III. The reaction temperature is not critical. At lower temperatures the reaction is slow, while at higher temperatures the production of side products is increased. The preferred reaction temperature is in the range of from about 10° C. to about 50° C., but it is most convenient to conduct the reaction at ambient temperature. The reaction time is not critical, and is dependent on reaction temperature. Normally a reaction time of from about twenty minutes to about three hours is utilized. At ambient temperature, a reaction time of about one hour is convenient and usually is sufficient to complete the reaction. The phthalimide which precipitates from the reaction mixture may then be extracted with a strong base (e.g. 10–20% aqueous KOH), and the organic solvent layer is dried, filtered and concentrated to yield the crude compound of Formula I. The reaction is conducted in a non-reactive organic solvent such as methylene chloride, chloroform, carbon tetrachloride, dimethylformamide, dimethylacetamide, tetrahydrofuran, diglyme, benzene, toluene, xylene or the like.

The compounds of Formula II utilized as starting materials in the process of this invention normally are isolated and stored as an acid addition salt, e.g. a trihydrochloride. The use of the acid addition salt is normally preferred when the reaction is conducted with sulfur monochloride or sulfur dichloride. Although the acid addition salt can be separately converted to its free base prior to reaction with the sulfur compound of Formula III, it is not necessary or desirable to do so. This preferably is done in situ simply by adding an appropriate amount of an organic base to a solution of the compound of Formula II prior to reaction with the compound of Formula III. Thus, for example, when utilizing 1 mole of a compound of Formula II as its trihydrochloride, one should add three moles of a suitable organic base. Suitable organic bases include tertiary amines such as trimethylamine, triethylamine, tri-n-propylamine, triisopropylamine, tri-n-butylamine, pyridine, N-methyl-morpholine, N-methylpiperidine, 1,4-diazabicyclo[2.2.2]-octane ("DABCO"), 1,8-diazabicyclo[5.4.0]undec-7-ene ("DBU"), 1,5-diazabicyclo-[4.3.0]non-5-ene ("DBN") and the like.

The compounds of Formula III may be readily prepared by the procedures described in *Can. J. Chem.*, 44, 2111–2113 (1966), *J. Am. Chem. Soc.*, 100, 1222–1228 (1978) and *Liebigs Ann. Chem.*, 121–136 (1982) in which R is

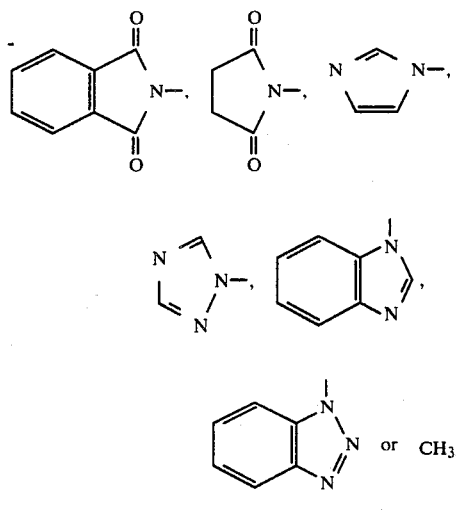

The most preferred compound of Formula III is N,N'-thiobisphthalimide.

In a preferred embodiment of the invention, the compounds of Formula I have the structure

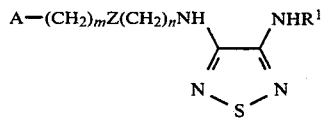

wherein $R^1$ is hydrogen, (lower)alkyl, allyl or propargyl, m is 0 or 1, n is 2 or 3, Z is oxygen, sulfur or methylene and A is imidazole, thiazole, thiadiazole, oxazole, oxadiazole or pyrimidine; provided that A is substituted by

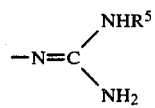

in which $R^5$ is hydrogen, or branched or unbranched (lower)alkyl group optionally substituted by one or more halogen atoms, provided that therre is no halogen atom on the carbon atom attached to the nitrogen atom; or a nontoxic pharmaceutically acceptable salt thereof.

In a more preferred embodiment, the compounds of Formula I have the structure

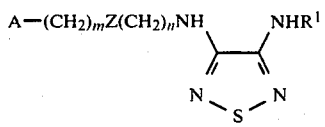

wherein $R^1$ is hydrogen or (lower)alkyl, m is 0 or 1, n is 2 or 3, Z is oxygen, sulfur or methylene and A is thiazole or pyrimidine; provided that A is substituted by

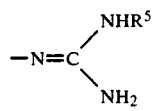

in which $R^5$ is hydrogen, or branched or unbranched (lower)alkyl group optionally substituted by one or more halogen atoms, provided that there is no halogen atom on the carbon atom attached to the nitrogen atom; or a nontoxic pharmaceutically acceptable salt thereof.

In another more preferred embodiment, the compounds of

Formula I have the structure

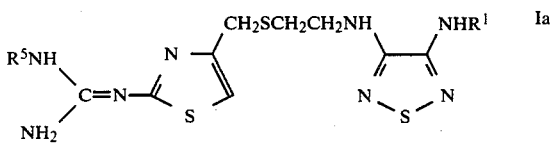

wherein $R^1$ is hydrogen or (lower)alkyl, and $R^5$ is hydrogen, or branched or unbranched (lower)alkyl group optionally substituted by one or more halogen atoms, provided that there is no halogen atom on the carbon atom attached to the nitrogen atom; or a nontoxic pharmaceutically acceptable salt thereof.

As presently envisaged, the most preferred compounds of Formula I are (1) 3-amino-4-{2-[(2-guanidinothiazol-4-yl)methylthio]ethylamino}-1,2,5-thiadiazole, (2) 3-amino-4-{2-[(2-{2-[2,2,2-trifluoroethyl]guanidino}thiazol-4-yl)methylthio]ethylamino}-1,2,5-thiadiazole, (3) 3-amino-4-{2-[(2-dimethylaminomethyl-4-thiazolyl)-methylthio]ethylamino}-1,2,5-thiadiazole, (4) 3-amino-4-{3-[4-guanidinopyrimidin-2-yloxy]-propylamino}-1,2,5-thiadiazole and (5) 3-amino-4-{3-[4-(2-{2,2,2-trifluoroethyl}guanidino)-pyrimidin-2-yloxy]propylamino}-1,2,5-thiadiazole.

The intermediates of Formula II used in the preparation of the compounds of Formula I may themselves be prepared by various procedures. In one procedure, the corresponding 3-(amino or substituted amino)-4-(substituted amino)-1,2,5-thiadiazole 1-oxide of Formula IV is treated with a strong mineral acid (preferably HCl) to produce the compound of Formula II.

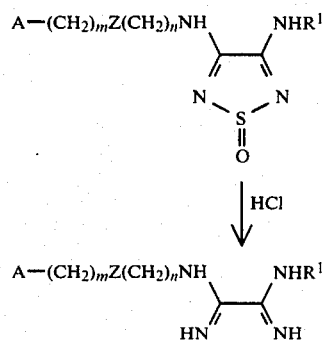

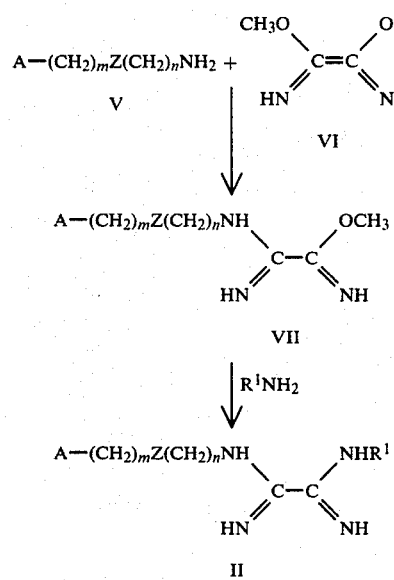

The reaction may be conducted in an inert solvent and preferably is conducted in methanol. Reaction temperature is not critical; it most conveniently is conducted at room temperature. The compounds of Formula IV are known or may readily be prepared by the procedures described in our U.S. Pat. No. 4,394,508.

In an alternate procedure, the compounds of Formula II may be prepared by the following reaction scheme. The reaction may be conducted in an inert solvent and preferably is conducted in methanol. The starting materials of Formula V are known or may be readily prepared by known procedures, e.g. as by procedures described in U.S. Pat. No. 4,394,508 and published European patent application Nos. 45,155 and 65,823.

In another aspect, this invention relates to novel intermediates of the formula

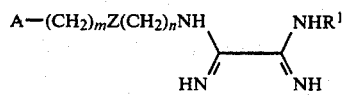

wherein $R^1$ is hydrogen, (lower)alkyl, 2-fluoroethyl, 2,2,2-trifluoroethyl, allyl, propargyl,

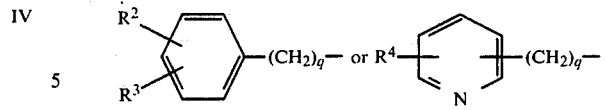

in which q is 1 or 2, $R^2$ and $R^3$ each are independently hydrogen, (lower)alkyl, (lower)alkoxy or halogen, and, when $R^2$ is hydrogen, $R^3$ also may be trifluoromethyl, or $R^2$ and $R^3$, taken together, may be methylenedioxy, and $R^4$ is hydrogen, (lower)alkyl or (lower)alkoxy;

m is an integer of from 0 to 2 inclusive;

n is an integer of from 2 to 5 inclusive;

Z is oxygen, sulfur or methylene; and

A is a 5- or 6-membered heterocyclic ring containing at least one nitrogen atom and one or two additional heteroatoms independently selected from oxygen, sulfur and nitrogen; provided that A may contain one or two substituents, the first substituent being selected from

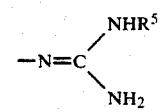

or

—$CH_2NR^6R^7$ and the second substituent selected from (lower)alkyl, halogen or (lower)alkoxy;

$R^5$ is hydrogen, or branched or unbranched (lower)alkyl, (lower)cycloalkyl, (lower)cycloalkyl(lower)alkyl, in which $R^5$ may optionally contain one or more halogen atoms selected from fluorine, chlorine and bromine, provided that there is no halogen substituent on the carbon atom directly attached to the nitrogen atom;

$R^6$ and $R^7$ each are independently hydrogen or (lower)alkyl, or, $R^6$ and $R^7$, taken together with the nitrogen to which they are attached, may be pyrrolidino, methylpyrrolidino, piperidino, methylpiperidino, homopiperidino or heptamethyleneimino, and a nontoxic pharmaceutically acceptable salt thereof.

In a preferred embodiment, the intermediates of Formula II have the structure

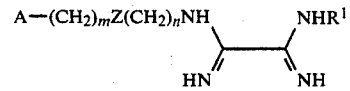

wherein $R^1$ is hydrogen, (lower)alkyl, allyl or propargyl, m is 0 or 1, n is 2 or 3, Z is oxygen, sulfur or methylene and A is imidazole, thiazole, thiadiazole, oxazole, oxadiazole or pyrimidine; provided that A is substituted by

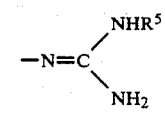

in which $R^5$ is hydrogen, or branched or unbranched (lower)alkyl group optionally substituted by one or moe halogen atoms, provided that there is no halogen atom on the carbon atom attached to the nitrogen atom; or a nontoxic pharmaceutically acceptable salt thereof.

In another preferred embodiment, the intermediates of Formula II have the structure

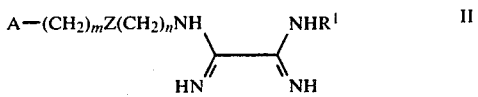

wherein $R^1$ is hydrogen or (lower)alkyl, m is 0 or 1, n is 2 or 3, Z is oxygen, sulfur or methylene and A is thiazole or pyrimidine; provided that A is substituted by

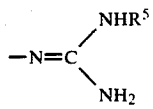

in which $R^5$ is hydrogen, or branched or unbranched (lower)alkyl group optionally substituted by one or more halogen atoms, provided that there is no halogen atom on the carbon atom attached to the nitrogen atom; or a nontoxic pharmaceutically acceptable salt thereof.

In another preferred embodiment, the intermediates of Formula II have the structure

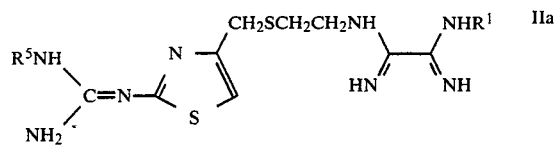

wherein $R^1$ is hydrogen or (lower)alkyl, and $R^5$ is hydrogen, or branched or unbranched (lower)alkyl group optionally substituted by one or more halogen atoms, provided that there is no halogen atom on the carbon atom attached to the nitrogen atom; or a nontoxic pharmaceutically acceptable salt thereof.

As presently envisaged, the most preferred intermediates of Formula II are (1) N-{2-[(2-guanidinothiazol-4-yl)methylthio]ethyl}ethanediimidamide,
(2) N-{2-[(2-{2-[2,2,2-trifluoroethyl]guanidino}thiazol-4-yl)methylthio]ethyl}ethanediimidamide,
(3) N-{2-[(2-dimethylaminomethyl-4-thiazolyl)methylthio]ethyl}ethanediimidamide,
(4) N-{3-[4-guanidinopyrimidin-2-yloxy]propyl}ethanediimidamide and
(5) N-{3-[4-(2-{2,2,2-trifluoroethyl}guanidino)pyrimidin-2-yloxy]propyl}ethanediimidamide;
and acid addition salts thereof.

In another embodiment, this invention includes pharmaceutical compositions comprising at least one compound of Formula I or a nontoxic pharmaceutically acceptable salt thereof in combination with a pharmaceutical carrier or diluent.

In another embodiment, this invention relates to a method of inhibiting gastric acid secretion in an animal in need thereof, which comprises administering to said animal an effective gastric acid inhibitory dose of at least one compound of Formula I, or a nontoxic pharmaceutically acceptable salt thereof.

For therapeutic use, the pharmacologically active compounds of Formula I will normally be administered as a pharmaceutical composition comprising as the (or an) essential active ingredient at least one such compound in its basic form or in the form of a nontoxic pharmaceutically acceptable acid addition salt, in association with a pharmaceutically acceptable carrier.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. The solid carrier may contain conventional excipients such as binding agents, fillers, tabletting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or nonaqueous liquid suspension, or may be a dry product for reconstitution with water or other suitable vehicle before use. Liquid preparations may contain conventional additives such as suspending agents, emulsifying agents, non-aqueous vehicle (including edible oils), preservatives, as well as flavoring and/or coloring agents. For parenteral administration, a vehicle normally will comprise sterile water, at least in large part, although saline solutions, glucose solutions and the like may be utilized. Injectable suspensions also may be used, in which case conventional suspending agents may be employed. Conventional preservatives, buffering agents and the like also may be added to the parenteral dosage forms. The pharmaceutical compositions are prepared by conventional techniques appropriate to the desired preparation.

The dosage of the compounds of this invention will depend not only on such factors as the weight of the patient, but also on the degree of gastric acid inhibition desired and the potency of the particular compound being utilized. The decision as to the particular dosage to be employed (and the number of times to be administered per day) is within the discretion of the physician, and may be varied by titration of the dosage to the particular circumstances of the specific patient. With the preferred compounds of this invention, each oral dosage unit will contain the active ingredient in an amount of from about 2 mg to about 300 mg, and most preferably from about 4 mg to about 100 mg. The active ingredient will preferably be administered in equal doses from one to four times a day.

Histamine $H_2$-receptor antagonists have been shown to be effective inhibitors of gastric secretion in animals, including man, Brimblecombe et al., *J. Int. Med. Res.*, 3, 86 (1975). Clinical evaluation of the histamine $H_2$-receptor antagonist cimetidine has shown it to be an effective therapeutic agent in the treatment of peptic ulcer disease, Gray et al., *Lancet*, 1, 8001 (1977). The preferred compound of this invention has been compared with cimetidine in various tests and has been found to be more potent than cimetidine both as an histamine $H_2$-receptor antagonist in isolated guinea pig right atria and as an inhibitor of gastric acid secretion in Heidenhain pouch dogs.

Histamine $H_2$-Receptor Antagonism-Isolated Guinea Pig Atria Assay

Histamine produces concentration-related increases in the contractile rate of isolated, spontaneously beating guinea pig right atria. Black et al., *Nature*, 236,, 385 (1972), described the receptors involved in this effect of histamine as histamine $H_2$-receptors when they reported the properties of burimamide, a competitive antagonist of these receptors. Subsequent investigations by Hughes and Coret, *Proc. Soc. Exp. Biol. Med.*, 148, 127 (1975) and Verma and McNeill, *J. Pharmacol. Exp. Ther.*, 200, 352 (1977) support the conclusion of Black and co-workers that the positive chronotropic effect of histamine in isolated guinea pig right atria is mediated via histamine $H_2$-receptors. Parsons et al., *Agents and Actions*, 7, 31 (1977) have shown that dimaprit, another specific $H_2$-agonist of the histamine $H_2$-receptors, can be utilized in place of histamine to stimulate the positive chronotropic effect in isolated guinea pig right atria. Black et al., *Agents and Actions*, 3, 133 (1973) and Brimblecombe et al., *Fed. Proc.*, 35, 1931 (1976) have utilized isolated guinea pig right atria as a means for comparing the activities of histamine $H_2$-receptor antagonists. The present comparative studies were carried out using a modification of the procedure reported by Reinhardt et al., *Agents and Actions*, 4, 217 (1974).

Male Hartley strain guinea pigs (350–450 gm) were sacrificed by cervical dislocation. The heart was excised and placed in a Petri dish of oxygenated (95% $O_2$, 5% $CO_2$) modified Krebs solution (g/liter: NaCl 6.6, KCl 0.35, $MgSO_4.7H_2O$ 0.295, $KH_2PO_4$ 0.162, $CaCl_2$ 0.238, $NaHCO_3$ 2.1 and dextrose 2.09). The spontaneously beating right atrium was dissected free from other tissues and a silk thread (4–0) attached to each end. The atrium was suspended in a 20 ml muscle chamber containing oxygenated modified Krebs solution maintained at 32° C. Atrial contractions were recorded isometrically by means of a Grass FT 03C force displacement transducer and recordings of contractile force and rate were made with a Beckman RP Dynograph.

A resting tension of 1 g was applied to the atrium and it was allowed to equilibrate for 1 hour. At the end of the equilibration period a submaximal concentration of histamine dihydrochloride ($1 \times 10^{-7}$ M) or dimaprit ($3 \times 10^{-7}$ M) was added to the bath and washed out to prime the tissue. Histamine or dimaprit was then added to the bath in a cumulative fashion using ½ log 10 intervals to give final molar bath concentrations of $3 \times 10^{-8}$ to $3 \times 10^{-5}$. The histamine-induced or dimaprit-induced increase in atrial rate was allowed to plateau before the next successive concentration was added. The maximal response invariably occurred at the $3 \times 10^{-5}$ M concentration. The histamine or dimaprit was washed out several times and the atrium allowed to return to control rate. The test compound was then added at appropriate molar concentrations and, after a 30-minute incubation, the histamine or dimaprit dose response was repeated adding higher concentrations as needed.

The dissociation constant ($K_B$) for cimetidine was derived from Schild plots by the method of Arunlakshana, O. and Schild, H. O. [*Br. J. Pharmacol.*, 14, 48 (1959)] using at least three dose levels. An estimate of the dissociation constant ($K_B$) for the compound of Example 1 at the dose utilized was determined by the method of Furchgott, R. F., *Ann. N.Y. Acad. Sci.*, 139, 553 (1967) from the formula $K_B$=concentration of antagonist/dose ratio−1. Parallel shifts in dose-response curves were obtained without depressing the maximal response at the concentrations utilized, and the results are shown in Table 1.

TABLE 1

| Activity in Isolated Guinea Pig Right Atria | | | |
|---|---|---|---|
| Compound | N | $K_B$ (μmoles) | Potency Ratio (cimetidine = 1.0) |
| cimetidine | 20 | 0.41 (0.21–0.64)* | 1.0 |

TABLE 1-continued

| Activity in Isolated Guinea Pig Right Atria | | | |
|---|---|---|---|
| Compound | N | $K_B$ (μmoles) | Potency Ratio (cimetidine = 1.0) |
| Example 1 | 5 | 0.0094 ± 0.0018** | 44 |

*95% confidence limits
**estimated dissociation constant ± S.E.
N = Number of preparations

Determination of Gastric Antisecretory Activity in the Heidenhain Pouch Dog

Prior to surgery, hematology and blood chemistry profiles are obtained and an assessment made as to the general health of selected female dogs. Dogs are vaccinated with Tissue Vax 5 (DHLP-Pitman-Moore) and housed in general animal quarters for four weeks' observation so incipient diseases may become apparent. Dogs are fasted with water ad libitum 24 hours prior to surgery.

Anesthesia is induced with Sodium Pentothal (Abbott) 25–30 mg/kg iv. Subsequent anesthesia is maintained with methoxyflurane (Pitman-Moore). A midline linea alba incision from xiphoid to umbilicus provides good exposure and ease of closure. The stomach is pulled up into the operative field, the greater curvature stretched out at multiple points and clamps placed along the selected line of incision. The pouch is made from the corpus of the stomach so that true parietal cell juice is obtained. About 30% of the corpus volume is resected. The cannula is made of light-weight, biologically-inert material such as nylon, Delrin or surgical stainless steel with dimensions and attachments after DeVito and Harkins [*J. Appl. Physiol.*, 14, 138 (1959)]. Post-operatively, dogs are medicated with antibiotics and an analgesic. They are allowed 2–3 months for recovery. Experiments are carried out in the following way: Dogs are fasted overnight (18 hours) with water ad libitum prior to each experiment. The dogs are placed in a sling and a saphenous vein cannulated for drug administration. Histamine as the base (100 μg/kg/hr) and chlorpheniramine maleate (0.25 mg/kg/hr) are infused continuously (in a volume of 6 ml/hr) with a Harvard infusion pump.

Ninety minutes' infusion are allowed for the dogs to reach a steady state of acid output. At this time the drug or normal saline (control) is administered concomitantly with the secretagogue in a volume of 0.5 ml/kg over a 30 second period. Infusion of the secretagogue is continued and 15 minute samples of the gastric juice are taken for 4.5 hours. Each sample is measured to the nearest 0.5 ml and tritratable acidity is determined by titrating a 1 ml sample to pH 7.0 with 0.2N NaOH, employing a fully automatic titration system (Metrohm). Titratable acid output is calculated in microequivalents by multiplying the volume in milliliters by the acid concentration in microequivalents per milliliter.

Results at peak activity after bolus intravenous administration of test compound are expressed as percent inhibition relative to control readings. Dose-response curves were constructed utilizing at least three dose levels with a minimum of three dogs at each dose level. The $ED_{50}$ values, potency ratios and 95% confidence limits, indicated in parentheses, were determined by Probit analysis according to Finney, D. J., "Probit Analysis" 3rd Edition, University Press, Cambridge, England, 1971, Chapter 4, and the results are shown in Table 2.

TABLE 2

Gastric Antisecretory Activity in the Histamine-Stimulated Heidenhain Pouch Dog

| Compound | $ED_{50}$ i.v.* ($\mu$moles/kg) | Potency Ratio (cimetidine = 1.0) |
|---|---|---|
| cimetidine | 2.6 (2.0–3.5) | 1.0 |
| Example 1 | 0.082 (0.055–0.12) | 32 |

*The intravenous dose giving 50% inhibition at the time of peak activity, i.e. 30 minutes post dose.

In addition to the results shown in Table 2, the antisecretory activity of the compound of Example 1 in the intravenous dog model shows a prolonged duration of action relative to cimetidine.

In the following examples, all temperatures are given in degrees Centigrade.

EXAMPLE 1

3-Amino-4-{2-[(2-guanidinothiazol-4-yl)methylthio]ethylamino}-1,2,5-thiadiazole cl A.
N-{2-[(2-Guanidinothiazol-4-yl)methylthio]ethyl}ethanediimidamide trihydrochloride A suspension of 3-amino-4-{2[(2-guanidinothiazol-4-yl)methylthio]ethylamino}-1,2,5-thiadiazole 1-oxide (5.25 g; 13.7 mmoles) [prepared according to published U.S. patent application No. 2,067,987] in 105 ml of methanol was treated with 80 ml of concentrated HCl to give an immediate yellow solution. After stirring at ambient temperature for 4.25 hours, the solution was concentrated to near dryness and the residue was triturated with acetone, filtered and dried to give the title compound.

B.
3-Amino-4-{2-[(2-guanidinothiazol-4-yl)methylthio]ethylamino}-1,2,5-thiadiazole A mixture of crude N-{2-[(2-guanidinothiazol-4-yl)methylthio]ethyl}ethanediimidamide trihydrochloride (5.65 g, 13.7 mmoles) [prepared in Step A], 50 ml of $CH_2Cl_2$ and 5.7 ml of triethylamine was treated with N,N'-thiobisphthalimide (DMF solvate) (5.44 g; 13.7 mmoles) and stirred for one hour to give a thick suspension. The mixture was treated with 40 ml of 2N NaOH and the solvents were decanted from the gum-like material which had separated. The gum was washed with 40 ml of 2N NaOH, water, and then dissolved in methanol and concentrated to give 3.0 g of crude product. The product was purified by flash chromatography on 90 g of silica gel (230–400 mesh) using ethyl acetate-methanol (97:3) as the eluent to give 2.44 g (54%) of the title compound. Treatment of the product in 35 ml of acetone with one equivalent of cyclohexylsulfamic acid gave the salt which was then recrystallized from 95% aqueous ethanol to give the title compound as its cyclohexylsulfamate salt, mp. 171°–173.5° C.

Anal. Calc'd for $C_9H_{14}N_8S_3 \cdot C_6H_{13}NO_3S$: C, 35.34; H, 5.34; N, 24.73; S, 25.16, Found: C, 35.39; H, 5.28; N, 24.23; S, 24.89

EXAMPLE 2

3-Amino-4-{2-[(2-{2-[2,2,2-trifluoroethyl]guanidino}thiazol-4-yl)methylthio]ethylamino}-1,2,5-thiadiazole When a suspension of 3-amino-4-{2-[(2-{2-[2,2,2-trifluoroethyl]guanidino}thiazol-4-yl)methylthio]ethylamino}-1,2,5-thiadiazole 1-oxide [prepared according to published U.S. patent application No. 65,823] is successively reacted according to the procedures of Example 1, Step A, and Step B, the title compound is thereby produced.

EXAMPLE 3

3-Amino-4-{2-[(2-dimethylaminomethyl-4-thiazolyl)-methylthio]ethylamino}-1,2,5-thiadiazole When a suspension of 3-amino-4-{2-[(2-dimethylaminomethyl-4-thiazolyl)methylthio]ethylamino}-1,2,5-thiadiazole 1-oxide [prepared according to the general procedures described in U.S. Pat. No. 4,394,508] is successively reacted according to the procedure of Example 1, Step A, and Step B, the title compound is thereby produced.

EXAMPLE 4

3-Amino-4-{3-[4-guanidinopyrimidin-2-yloxy]-propylamino}-1,2,5-thiadiazole

When a suspension of 3-amino-4-{3-[4-guanidinopyrimidin-2-yloxy]propylamino}-1,2,5-thiadiazole 1-oxide [prepared according to the general procedures described in U.S. Pat. Nos. 4,394,508 and 4,362,728] is successively reacted according to the procedure of Example 1, Step A, and Step B, the title compound is thereby produced.

EXAMPLE 5

3-Amino-4-{3-[4-(2-{2,2,2-trifluoroethyl}guanidino)-pyrimidin-2-yloxy]propylamino}-1,2,5-thiadiazole When a suspension of 3-amino-4-{3-[4-(2-{2,2,2-trifluoroethyl}guanidino)pyrimidin-2-yloxy]propylamino}-1,2,5-thiadiazole 1-oxide [prepared according to the general procedures described in U.S. Pat. Nos. 4,394,508 and 4,362,728] is successively reacted according to the procedure of Example 1, Step A, and Step B, the title compound is thereby produced.

EXAMPLE 6

The general procedure of Example 1, Step A and Step B, is repeated except that the 3-amino-4-{2-[(2-guanidinothiazol-4-yl)methylthio]ethylamino}-1,2,5-thiadiazole 1-oxide utilized therein is replaced by an equimolar amount of 3-amino-4-{4-[2-(2-{2,2,2-trifluoroethyl}guanidino)-thiazol-4-yl]butylamino}-1,2,5-thiadiazole 1-oxide, 3-amino-4-{5-[2-(2-{2,2,2-trifluoroethyl}guanidino)-thiazol-4-yl]pentylamino}-1,2,5-thiadiazole 1-oxide, 3-amino-4-{4-[2-guanidino-4-oxazolyl]butylamino}-1,2,5-thiadiazole 1oxide, 3-amino-4-{2-[(5-guanidino-1,2,4-thiadiazol-3-yl)methylthio]ethylamino}-1,2,5-thiadiazole 1-oxide, 3-amino-4-{2-[2,2,2-trifluoroethyl]guanidino]-1,2,4-thiadiazol-3-yl)methylthio]ethylamino}-1,2,5-thiadiazole 1-oxide, 3-amino-4-{4-[4-guanidinopyrimidin-2-yl]butylamino}-1,2,5-thiadiazole 1-oxide, 3-amino-4-{4-[4-(2-{2,2,2-trifluoroethyl}guanidino)-pyrimidin-2-yl]butylamino}-1,2,5-thiadiazole 1-oxide, 3-amino-4-{3-[4-guanidinopyrimidin-2-ylthio]-propylamino}-1,2,5-thiadiazole 1-oxide, 3-amino-4-{3-[4-(2-{2,2,2-trifluoroethyl}guanidino)-pyrimidin-2-ylthio]propylamino}-1,2,5-thiadiazole 1-oxide, 3-amino-4-{4-[4-guanidinopyrimidin-2-yl]butylamino}-1,2,5-thiadiazole 1-oxide, 3-amino-4-{4-[4-(2-{2,2,2-trifluoroethyl}guanidino)-pyrimidin-2-yl]butylamino}-1,2,5-thiadiazole 1-oxide, 3-amino-4-{2-[(4-guanidinopyrimidin-2-yl)methylthio]ethylamino}-1,2,5-thiadiazole 1-oxide, 3-amino-4-{2-[(4-{2-[2,2,2-trifluoroethyl]guanidino}pyrimidin-2-yl)methylthio]ethylamino}-1,2,5-thiadiazole 1-oxide, 3-amino-4-{3-[4-(2-{2-ethyl}guanidino)pyrimidin-2-yloxy]propylamino}-1,2,5-thiadiazole 1-oxide and 3-amino-4-{3-[4-(2-{3-propyl}guanidino)pyrimidin-2-yloxy]propylamino}-1,2,5-thiadiazole 1-oxide, respectively, [each prepared by the general procedures described in U.S. Pat. No. 4,394,508 and No. 4,362,728]

and there is thereby produced 3-amino-4-{4-[2-(2-{2,2,2-trifluoroethyl}guanidino)-thiazol-4-yl]butylamino}-1,2,5-thiadiazole, 3-amino-4-{5-[2-(2-{2,2,2-trifluoroethyl}guanidino)-thiazol-4-yl]pentylamino}-1,2,5-thiadiazole, 3-amino-4-{4-[2-guanidino-4-oxazolyl]butylamino}-1,2,5-thiadiazole, 3-amino-4-{2-[(5-guanidino-1,2,4-thiadiazol-3-yl)methylthio]ethylamino}-1,2,5-thiadiazole, 3-amino-4-{2-[(5-{2-[2,2,2-trifluoroethyl]guanidino}-1,2,4-thiadiazol-3-yl)methylthio]ethylamino}-1,2,5-thiadiazole, 3-amino-4-{4-[4-guanidinopyrimidin-2-yl]butylamino}-1,2,5-thiadiazole, 3-amino-4-{4-[4-(2-{2,2,2-trifluoroethyl}guanidino)-pyrimidin-2-yl]butylamino}-1,2,5-thiadiazole, 3-amino-4-{3-[4-guanidinopyrimidin-2-ylthio]propylamino}-1,2,5-thiadiazole, 3-amino-4-{3-[4-(2-{2,2,2-trifluoroethyl}guanidino)-pyrimidin-2-ylthio]propylamino}-1,2,5-thiadiazole, 3-amino-4-{4-[4-guanidinopyrimidin-2-yl]butylamino}-1,2,5-thiadiazole, 3-amino-4-{4-[4-(2-{2,2,2-trifluoroethyl}guanidino)-pyrimidin-2-yl]butylamino}-1,2,5-thiadiazole, 3-amino-4-{2-[(4-guanidinopyrimidin-2-yl)methylthio]ethylamino}-1,2,5-thiadiazole, 3-amino-4-{2-[(4-{2-[2,2,2-trifluoroethyl]guanidino}pyrimidin-2-yl)methylthio]ethylamino}-1,2,5-thiadiazole, 3-amino-4-{3-[4-(2-{2-ethyl}guanidino)pyrimidin-2-yloxy]propylamino}-1,2,5-thiadiazole and 3-amino-4-{3-[4-(2-{3-propyl}guanidino)pyrimidin-2-yloxy]propylamino}-1,2,5-thiadiazole, respectively.

EXAMPLE 7

The general procedure of Example 1, Step A and Step B, is repeated except that the 3-amino-4-{2-[(2-guanidinothiazol-4-yl)methylthio]ethylamino}-1,2,5-thiadiazole 1-oxide utilized therein is replaced by an equimolar amount of 3-methylamino-4-{2-[(2-guanidinothiazol-4-yl)methylthio]ethylamino}-1,2,5-thiadiazole 1-oxide, 3-allylamino-4-{2-[(2-guanidinothiazol-4-yl)methylthio]ethylamino}-1,2,5-thiadiazole 1-oxide, 3-(2-propynyl)amino-4-{2-[(2-{2-[2,2,2-trifluoroethyl]-guanidino}thiazol-4-yl)methylthio]ethylamino}-1,2,5-thiadiazole 1-oxide, 3-propylamino-4-{3-[4-guanidinopyrimidin-2-yloxy]-propylamino}-1,2,5-thiadiazole 1-oxide, 3-benzylamino-4-{3-[4-(2-{2,2,2-trifluoroethyl}guanidino)pyrimidin-2-yloxy]propylamino}-1,2,5-thiadiazole 1-oxide, 3-(3,4-dimethyloxybenzylamino)-4-{2-[(2-{2-[2,2,2-trifluoroethyl]-guanidino}thiazol-4-yl)methylthio]ethylamino}-1,2,5-thiadiazole 1-oxide, 3-[(3-pyridyl)methylamino]-4-{4-[2-{2,2,2-trifluoroethyl}guanidino)pyrimidin-2-yl]butylamino}-1,2,5-thiadiazole 1-oxide and 3-[(6-methyl-3-pyridyl)methylamino]-4-{3-[4-(2-{2,2,2-trifluoroethyl}guanidino)pyrimidin-2-ylthio]-propylamino}-1,2,5-thiadiazole 1-oxide, respectively, [each prepared by the general procedures described in U.S. Pat. Nos. 4,394,508 and 4,362,728]

and there is thereby produced 3-methylamino-4-{2-[(2-guanidinothiazol-4-yl)methylthio]ethylamino}-1,2,5-thiadiazole, 3-allylamino-4-{2-[(2-guanidinothiazol-4-yl)methylthio]ethylamino}-1,2,5-thiadiazole, 3-(2-propynyl)amino-4-{2-[(2-{2-[2,2,2-trifluoroethyl]-guanidino}thiazol-4-yl)methylthio]ethylamino}-1,2,5-thiadiazole, 3-propylamino-4-{3-[4-guanidinopyrimidin-2-yloxy]-propylamino}-1,2,5-thiadiazole, 3-benzylamino-4-{3-[4-(2-{2,2,2-trifluoroethyl}guanidino)pyrimidin-2-yloxy]propylamino}-1,2,5-thiadiazole, 3-(3,4-dimethyloxybenzylamino)-4-{2-[(2-[2,2,2-trifluoroethyl]guanidino}thiazol-4-yl)methylthio]ethylamino}-1,2,5-thiadiazole, 3-[(3-pyridyl)methylamino]-4-{4-[2-{2,2,2-trifluoroethyl}guanidino)pyrimidin-2-yl]butylamino}-1,2,5-thiadiazole and 3-[(6-methyl-3-pyridyl)methylamino]-4-{3-[4-(2-{2,2,2-trifluoroethyl}guanidino)pyrimidin-2-ylthio]-propylamino}-1,2,5-thiadiazole, respectively.

We claim:

1. A compound of the formula $$A-(CH_2)_mZ(CH_2)_nNH\diagdown\diagup NHR^1 \qquad II$$
$$HN=\diagup\diagdown=NH$$

wherein $R^1$ is hydrogen, (lower)alkyl, 2-fluoroethyl, 2,2,2-trifluoroethyl, allyl, propargyl,

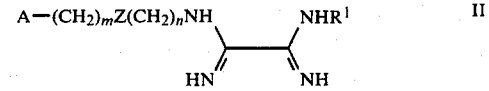

in which q is 1 or 2, $R^2$ and $R^3$ each are independently hydrogen, (lower)alkyl, (lower)alkoxy or halogen, and, when $R^2$ is hydrogen, $R^3$ also may be trifluoromethyl, or $R^2$ or $R^3$, taken together, may be methlenedioxy, and $R^4$ is hydrogen, (lower)alkyl or (lower)alkoxy:

m is an integer of from 0 to 2 inclusive;

n is an integer of from 2 to 5 inclusive;

Z is oxygen, sulfur or methylene; and

A is a imidazole, thiazole, thiadiazole, oxazole, oxadiazole or pyrimidine; provided that A may contain one or two substituents, the first substituent being selected from

or —CH$_2$NR$^6$R$^7$ and the second substituent selected from (lower)alkyl, halogen or (lower)alkoxy;

R$^5$ is hydrogen, branched or unbranched (lower)alkyl, (lower)cycloalkyl, or (lower)cycloalkyl(lower)alkyl, in which R$^5$ may optionally contain one or more halogen atoms selected from fluorine, chlorine and bromine, provided that there is no halogen substituent on the carbon atom directly attached to the nitrogen atom;

R$^6$ and R$^7$ each are independently hydrogen or (lower)alkyl, or, R$^6$ and R$^7$, taken together with the nitrogen to which they are attached, may be pyrrolidino, methylpyrrolidino, piperidino, methylpiperidino, homopiperidino or heptamethyleneimino, and a nontoxic pharmaceutically acceptable salt thereof.

2. A compound of claim 1 having the formula

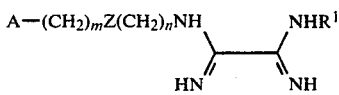
II wherein R$^1$ is hydrogen, (lower)alkyl, allyl or propargyl, m is 0 or 1, n is 2 or 3, Z is oxygen, sulfur or methylene and A is imidazole, thiazole, thiadiazole, oxazole, oxadiazole or pyrimidine; provided that A is substituted by

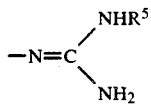

in which R$^5$ is hydrogen, or branched or unbranched (lower)alkyl group optionally substituted by one or more halogen atoms, provided that there is no halogen atom on the carbon atom attached to the nitrogen atom; or a nontoxic pharmaceutically acceptable salt thereof.

3. A compound of claim 1 having the formula

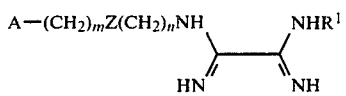
II wherein R$^1$ is hydrogen or (lower)alkyl, m is 0 or 1, n is 2 or 3, Z is oxygen, sulfur or methylene and A is thiazole or pyrimidine; provided that A is substituted by

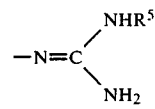

in which R$^5$ is hydrogen, or branched or unbranched (lower)alkyl group optionally substituted by one or more halogen atoms, provided that there is no halogen atom on the carbon atom attached to the nitrogen atom; or a nontoxic pharmaceutically acceptable salt thereof.

4. A compound of claim 1 having the formula

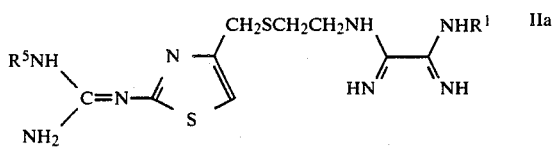
IIa wherein R$^1$ is hydrogen or (lower)alkyl, and R$^5$ is hydrogen, or branched on unbranched (lower)alkyl group optionally substituted by one or more halogen atoms, provided that there is no halogen atom on the carbon atom attached to the nitrogen atom; or a nontoxic pharmaceutically acceptable salt thereof.

5. N-{2-[(2-Guanidinothiazol-4-yl)methylthio]ethyl}ethanediimidamide, or a nontoxic pharmaceutically acceptable salt thereof.

* * * * *